(12) United States Patent
Camborde et al.

(10) Patent No.: US 6,566,361 B2
(45) Date of Patent: *May 20, 2003

(54) AZAPIRONE PAIN TREATMENT

(75) Inventors: Francoise Camborde, Orsay (FR); Alix Cloarec, Triel sur Seine (FR); Charles Conway, Cheshire, CT (US)

(73) Assignees: Laboratories, UPSA (FR); Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/860,181

(22) Filed: May 17, 2001

(65) Prior Publication Data

US 2002/0032215 A1 Mar. 14, 2002

Related U.S. Application Data

(63) Continuation-in-part of application No. 09/754,766, filed on Jan. 4, 2001, which is a continuation-in-part of application No. PCT/FR00/01817, filed on Jun. 29, 2000.

(30) Foreign Application Priority Data

Jun. 30, 1999 (FR) .............................. 99 08363

(51) Int. Cl.$^7$ ............................................ A61K 31/497
(52) U.S. Cl. .......................... 514/252.14; 514/252.15; 514/252.16; 514/252.17; 514/252.18; 514/252.19; 514/922
(58) Field of Search ....................... 514/252.14, 252.15, 514/252.16, 252.17, 252.18, 252.19, 922

(56) References Cited

U.S. PATENT DOCUMENTS

| 3,717,634 A | 2/1973 | Wu et al. |
| 4,182,763 A | 1/1980 | Casten et al. |
| 4,423,049 A | 12/1983 | Temple, Jr. |
| 4,435,405 A | 3/1984 | Blackburn et al. |
| 4,507,303 A | 3/1985 | Ishizumi et al. |
| 4,576,953 A | 3/1986 | Le Count |
| 4,607,039 A | 8/1986 | Le Count et al. |
| 4,794,112 A | 12/1988 | Cooper |
| 5,872,145 A | 2/1999 | Plachetka |

FOREIGN PATENT DOCUMENTS

| EP | 129128 | 11/1990 |
| GB | 2222768 | 3/1990 |

OTHER PUBLICATIONS

Giordano, et al., "Antinociceptive effect of the novel anxiolytic buspirone in three pain tests in rats," *Pain*, 39, 1989, 109–113.
Giordano, et al., "Putative mechanisms of buspirone–induced antinociception in the rat," *Pain*, 50, 1992, 365–372.
Kishore–Kumar, et al., "Single doses of the serotonin agonists buspirone and m–chlorophenylpiperazine do not relieve neuropathic pain," *Pain*, 37, 1989, 223–227.
Cao, et al., "Buspirone and 1–(2–pyrimidinyl)–piperazine attenuate xylazine–induced antinociception in the mouse," *J. Pharm. Pharmacol.*, 1994, 46, 931–932.
Pascual, et al., "Buspirone in primary headaches," *Acta. Neurol. Scand.*, 1998, 97, 142.
Woodbury, et al., "Analgesic–antipyretics, Anti–Inflammatory Agents, and Drugs Employed in the Therapy of Gout," *The Pharmacologic Basis of Therapeutics*, 5th edition, Macmillan Publishing Co., 1975, 325–358.
Abou–Garcia, et al., Polycyclic Aryl– and Heteroarylpiperazinyl Imides as 5–HT1A Receptor Ligands and Potential Anxiolytic Agents: Synthetis and Structure–Activity Relationship Studies, *J. Med. Chem.*, 1988, 31, 1382–1392.

*Primary Examiner*—Frederick Krass
(74) *Attorney, Agent, or Firm*—Richard P. Ryan

(57) ABSTRACT

A method of treating pain with acetaminophen comprises the concurrent administration of an azapirone such as buspirone. This combination of agents surprisingly results in a strengthened analgesic response characterized by rapid onset, greater pain relief, and a longer duration of action.

26 Claims, 8 Drawing Sheets

COADMINISTRATION OF BUSPIRONE AND ACETAMINOPHEN IN ACUTE PAIN TESTING

Coadministration yields greater analgesic efficacy

COADMINISTRATION OF BUSPIRONE AND ACETAMINOPHEN IN ACUTE PAIN TESTING

COADMINISTRATION OF BUSPIRONE AND ACETAMINOPHEN IN CHRONIC PAIN TESTING

COADMINISTRATION OF BUSPIRONE AND ACETAMINOPHEN IN NEUROPATHIC PAIN TESTING

COADMINISTRATION OF GEPIRONE AND ACETAMINOPHEN IN ACUTE PAIN TESTING

Dunnett's test:
  */** $p<0.05/.01$ (Gepirone+Acetaminophen vs vehicle)
  °/°° $P<0.05/.01$ (Acetaminophen+saline vs vehicle)
  +/++ $P<0.05/.01$ (Gepirone+PETW vs vehicle)

COADMINISTRATION OF IPSAPIRONE AND ACETAMINOPHEN IN ACUTE PAIN TESTING n=6 per group Dunnett's test:
    */** $p<0.05/.01$ (Ipsapirone+Acetaminophen vs vehicle)
    °/°° $P<0.05/.01$ (Acetaminophen+dH2O vs vehicle)
    +/++ $P<0.05/.01$ (Ipsapirone+PETW vs vehicle)

COADMINISTRATION OF TANDOSPIRONE AND ACETAMINOPHEN IN ACUTE PAIN TESTING n=6 per group Dunnett's test:
  */** p<0.05/.01 (Tandospirone+Acetaminophen vs vehicle)
  °/°° P<0.05/.01 (Acetaminophen+DMA/PETW vs vehicle)
  +/++ P<0.05/.01 (Tandospirone+DMA/PETW vs vehicle)

AZAPIRONE PAIN TREATMENT

CROSS REFERENCE TO RELATED APPLICATION

This continuation-in-part application claims priority from U.S. Ser. No. 09/754,766 filed Jan. 4, 2001 which itself is a continuation-in-part application of PCT/FR00/01817 filed Jun. 29, 2000 which claims priority from French patent application 99.08363 filed Jun. 30, 1999.

BACKGROUND OF THE INVENTION

This invention relates to the use of a therapeutic combination of two compounds to treat pain. The method of pain treatment comprises co-administration of an azapirone with acetaminophen (paracetamol). This combination of agents produces a more robust opioid-type analgesia providing more rapid onset and/or longer duration.

Acetaminophen is an established analgesic agent having only weak anti-inflammatory activity and can be classified as a non-NSAID analgesic. Ibuprofen is an example of a non-steroidal analgesic having significant anti-inflammatory properties and is classified as a non-steroidal anti-inflammatory drug (NSAID). Acetaminophen is believed to relieve pain by elevation of the pain threshold and is generally given in amounts ranging from about 600 to 1300 mg per dose in humans.

While acetaminophen is equally effective as aspirin, it is unlikely to produce many of the adverse effects of aspirin and aspirin-containing products. Acetaminophen itself, however, has been associated with a propensity for contributing to liver damage in patients that ingest significant amounts of alcohol. The dose-related toxic effect of acetaminophen on liver is demonstrated by the hepatic toxicity seen with overdosage of acetaminophen. Therefore, it would be desirable to be able to effectively treat pain utilizing lower doses of acetaminophen.

Combinations of various analgesics to provide additive effects in treating pain are known in the literature; e.g., combinations of aspirin with codeine or other narcotic analgesics are known to provide additive analgesic effects in man. See: *The Pharmacologic Basis of Therapeutics, 5th* edition, Macmillan Publishing Co., 1975, pp. 325–358. More active analgesic combinations are continually sought since they may be able to relieve pain with reduced dosages, thereby diminishing accompanying adverse effects and toxicities resulting from higher dosages. It is particularly desirable to discover a potentiating agent and/or a synergistic combination effect. The present invention concerns the concurrent administration of an azapirone with acetaminophen to provide increased analgesic effects.

Acetaminophen combinations have been previously disclosed.

Cooper, in U.S. Pat. No. 4,794,112 disclosed combinations of hydroxyzine with acetaminophen as being effective analgesic compositions.

Certain azapirone compounds and their pharmaceutically acceptable salts have been described as being useful in treating anxiety and depression disorders. These compounds have general structure (I) and are identified below.

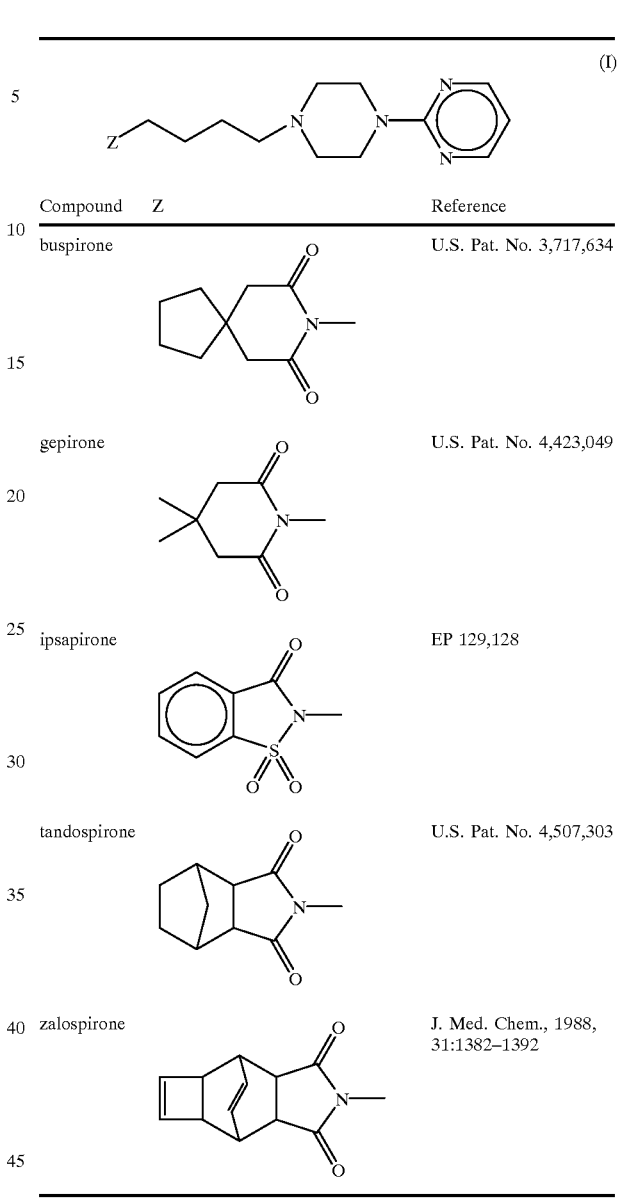

These particular azapirones contain the pyrimidinylpiperazine moiety as an integral part of their molecular structure. The most studied and well-known member of this compound class is buspirone.

Buspirone, chemically: 8-[4-[4-(2-pyrimidinyl)1-piperazinyl]butyl-8-azaspiro(4,5)-decane-7,9-dione, is a pharmaceutically active compound which was disclosed in U.S. Pat. No. 4,182,763 as being effective for the treatment of anxiety mixed with depression. A number of other pharmacologic actions useful in treating various clinical disorders have been reported for buspirone. Antinociceptive effects of buspirone have been described in numerous references. For example, Giordano, et al., 1989, *Pain*, 39, 109–113, suggest the potential use of buspirone in treating pain arising from chemical and mechanical nociception.

Additional study of buspirone-induced antinociception by Giordano et al., 1992, *Pain*, 50, 365–372, concluded that buspirone produced a non-opioid type of analgesia.

Roberts, et al., in GB 2,222,768 disclose and claim the use of 5-HT1-like agonists as analgesics. A group of specifically disclosed agents classified as agonists, including buspirone, were reported as being expected to exhibit analgesic activity to a greater or lesser extent than the 5-HT1 agonist 8-hydroxy-DPAT.

A study on neuropathic pain by Kishare-Kumar, et al., reported in *Pain*, 1989, 37, 223–227, indicated that acute high doses of buspirone did not relieve neuropathic pain.

Combining buspirone with other analgesic has been disclosed by B. -J. Cao, et al., in *J. Pharm. Pharmacol.*, 1994, 46, 331–332, where buspirone was demonstrated as acting to attenuate xylazine-induced antinociception. These studies were prompted by the earlier reports of buspirone's attenuation of antinociception induced by morphine and sufentanil. These reports teach away from the use of buspirone to potentiate the analgesic effect of another pain-relieving agent.

Plachetka in U.S. Pat. No. 5,872,145 discloses a method of treating migraine by the co-timely administration of a 5-HT agonist and a NSAID or non-NSAID analgesic agent. While acetaminophen is listed as an example of such a non-NSAID, buspirone is not mentioned in the patent. The intended 5-HT1 agonist prototype is sumatriptan, a member of a different 5-HT1 subclass than buspirone.

Buspirone, by itself, has been reported to be useful in the preventive treatment of headaches. Cf: Pascual, et al., *Acta. Neurol. Scand.*, 1998, 97, 142.

Buspirone is commercially available from Bristol-Myers Squibb Company for the treatment of anxiety. Use in pain management is not an approved indication for buspirone.

In summary, the prior art does not disclose or suggest the novel use of an azapirone such as buspirone to strengthen the analgesic effect of acetaminophen. The concurrent administration of an azapirone such as buspirone with acetaminophen provides a qualitative improvement in the resulting analgesia. In the case of buspirone, the onset, duration and degree of analgesia produced is morphine-like and as such is unexpected, particularly in view of reports of buspirone's attenuation of the antinociceptive effects of certain analgesics.

SUMMARY OF THE INVENTION

The present invention provides a method for treatment of pain comprising the concurrent administration of azapirones such as buspirone and acetaminophen in a manner which results in strengthening of the antinociceptive effects of acetaminophen. The analgesia produced by the concurrent administration of acetaminophen and azapirones such as buspirone is qualitatively opioid-like, resembling morphine in having a rapid onset, providing greater pain relief and maintaining the analgesic effect for a longer time. The addition of an azapirone such as buspirone also allows for the use of smaller amounts of acetaminophen, thereby reducing the liver toxicity potential. The present invention also comprises pharmaceutical compositions and pharmaceutical kit/packaging containing acetaminophen and an azapirone such as buspirone for combination therapy.

DETAILED DESCRIPTION OF THE INVENTION

Figure 1:
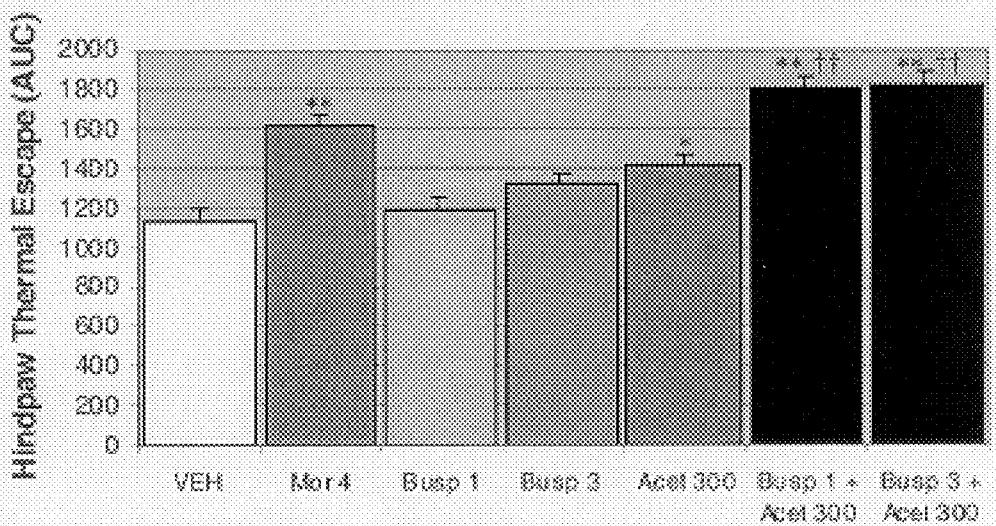
FIG. 1 Buspirone (1 or 3 mg/kg; ip) potentiates the analgesic effect of acetaminophen (300 mg/kg; ip). The hindpaw thermal escape response of albino rats was elevated significantly above vehicle (Veh) by acetaminophen (Acet 300 mg/kg; ip). When buspirone (1 or 3 mg/kg; ip) was co-administered with acetaminophen (Busp 1+Acet 300, and Busp 3+Acet 300) the analgesic effect was greater than either compound given alone, and also exceeded that of morphine (Mor 4 mg/kg; ip). Data are expressed as mean±sem for Area Under the Curve (AUC) as calculated from thermal escape latencies (sec) over 120 min post injection period. *p<0.05**p<0.01 compared to Veh, ††p<0.01 compared to single dose components.

In accordance with the present invention, pain is relieved in mammals by concurrent systemic administration of acetaminophen and an azapirone such as buspirone or an acid salt form thereof in an amount sufficient to significantly strengthen the analgesic activity of the acetaminophen. While the azapirone component may be selected from buspirone, gepirone, ipsapirone, tandospirone or zalospirone; buspirone is most preferred and will be used as the exemplary azapirone in describing the present invention.

The addition of buspirone to acetaminophen administration has been found to produce a marked potentiation of acetaminophen's analgesic effects. This combination therapy of buspirone with acetaminophen results in an enhanced therapeutic effect similar to morphine allowing for greater and longer-lasting efficacy with a faster onset of action. By potentiating acetaminophen's analgesic effects, lower doses can be employed to limit the potential for adverse effects. Moreover, acetaminophen potentiated with buspirone can be used to treat severe pain for which acetaminophen alone would not be effective. Thus, this method of pain treatment widens the use of acetaminophen to treat pain of varied origins in a much larger number of patients. The present method of pain treatment is also intended for application to animals.

As used herein, the term "animal" shall refer to a vertebrate animal. More preferably, the vertebrate animal is a mammal. As used herein, the term "mammal" shall refer to the Mammalia class of higher vertebrates. The term "mammal" includes, but is not limited to, a human. The term "treating" as used herein includes prophylaxis of the named condition or amelioration or elimination of the condition and/or its characteristic symptoms once it has been established.

As used herein, the term "pain" shall refer to all types of pain. Preferably, the term shall refer to acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis, the term shall also preferredly refer to nociceptive pain or nociception.

By "therapeutically effective amount" is meant an amount of acetaminophen that when administered alone is effective in providing pain relief. "Concurrent administration," "administered in combination" or similar phrases referring to the acetaminophen and azapirone components mean that the components are administered concurrently to the mammal being treated. By "concurrently," it is meant that each component may be administered at the same time or sequentially in any order at different points in time. However, if not administered at the same time, they should be administered sufficiently closely in time so as to provide the desired potentiation of treatment effect. Suitable dosing intervals and dosing order with such compounds will be readily apparent to those skilled in the art, once armed with the present disclosure. Preferably both components are administered at the same time or within an hour of each other.

The mechanism of action for azapirones such as buspirone is not completely understood. At present, buspirone is believed to act as an agonist at pre-synaptic 5-HT1A receptors and as a partial agonist/antagonist at post-synaptic 5-HT1A receptors. It also has agonistic action at presynaptic D2 dopaminergic receptors. Acetaminophen is believed to act by elevating the pain threshold in patients. With respect to the azapirone-APAP combination, rat plasma concentrations of buspirone and APAP over time do not differ significantly whether given alone or in combination. This demonstrates that the strengthened analgesic effect is not due to a pharmacokinetic effect.

Acetaminophen by itself is generally given in analgesic doses ranging from about 300 to 1300 mg and preferably from about 650 to 1300 mg with a maximum recommended daily dose of about 4000 mg. As an anxiolytic, buspirone is generally given in doses of 5 to 30 mg with recommended daily doses of about 10 to 60 mg and usually about 20 to 40 mg. The other azapirones have not had recommended doses established.

For concurrent administration in the present method of pain treatment, acetaminophen doses would be no lower than the minimally effective dose (MED) for effective analgesia. It is expected that the unit azapirone dose would generally be below 30 mg. There has been no clinical dose established for any azapirone other than buspirone and no clinical dose has been established for buspirone's use as a single agent to treat pain. The azapirone component is preferably employed in acid addition salt form; e.g., the hydrochloride salt form for buspirone.

The precise therapeutic dose of the individual component agents, acetaminophen and azapirone, as well as the amount of a pharmaceutical combination formulation may depend on several variables. Some of these would be: azapirone selected, route of administration, time of drug release (e.g., instant or extended), administration schedule, pain severity, condition of the patient, and the like. With respect to acetaminophen, it will be concurrently administered with the effective analgesic strengthening amount of an azapirone (or its acid salts) in a total combined pain relieving amount, in doses given 1 to 6 times a day as needed to relieve pain. In general, it is desirable to employ at least an amount of acetaminophen that by itself would be minimally effective in producing analgesia. Suitable per dose amounts for acetaminophen component are from 200 to 1300 mg, but are preferably from 500 to 1000 mg.

In Table 1 are shown general and preferred dose ranges of acetaminophen, azapirone, and the weight ratio range.

TABLE 1

| | Acetaminophen Dose Range | Azapirone (HCl) Dose Range | Azapirone:Acetaminophen Weight Ratio Range |
|---|---|---|---|
| General | 200–1300 | 0.5–30 | 1:5 to 1:2600 |
| Particular | 500–1000 | 1.0–20 | 1:25 to 1:1000 |
| More particular | 650–1000 | 5.0–10 | 1:65–1:200 |

Consequently, the weight ratio of acetaminophen to azapirone, while selected to provide the highest level of analgesic strengthening, would be generally from about 5:1 to 2600:1 and particularly about 25:1 to 1000:1.

The analgesic strengthening effect has been demonstrated in accepted rodent pain models.

Using a mouse hot plate test procedure described by Eddy, et al., in *J. Pharmacol. Exp. Ther.,* 1950, 98:121–137; buspirone demonstrated potentiation of acetaminophen at buspirone to acetaminophen weight ratios of 1:3, 1:10, and 1:30.

More definitive testing was done using the rat hindpaw thermal escape paradigm which is described in more detail infra. The results of these tests are displayed in FIGS. 1 to 3, 6 to 8.

FIG. 1 demonstrates the potentiating effect of 1 and 3 mg/kg buspirone HCl on a 300 mg/kg analgesic dose of acetaminophen.

Figure 2:
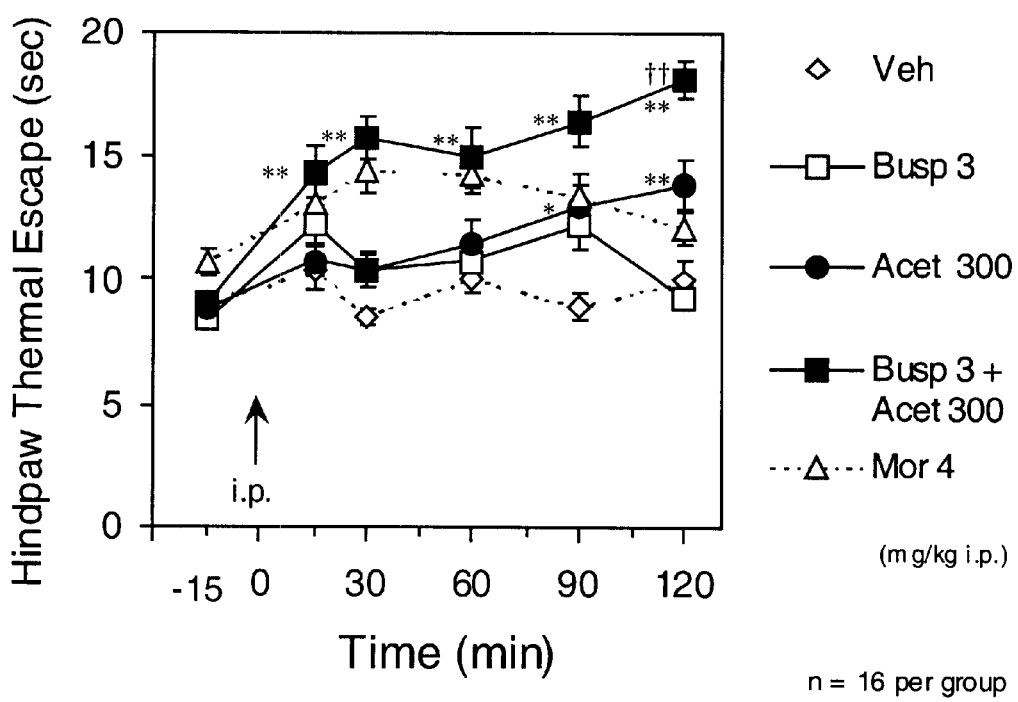
FIG. 2 Coadministration of Buspirone (3 mg/kg; ip) and Acetaminophen (300 mg/kg; ip) produces faster onset and longer lasting efficacy compared to Acetaminophen alone. The hindpaw thermal escape latency of albino rats was elevated significantly above vehicle (--- ◊ ---) at 90 and 120 min for acetaminophen (Acet 300 mg/kg; ip-●-). When buspirone (3 mg/kg; ip-□-) was co-administered with acetaminophen (Busp 3+Acet 300-■-) the analgesic onset was significantly shortened to 15 min post injection. Further, the efficacy of the combination was greater than acetaminophen alone throughout the 2 hr post-injection period, and exceeded that of morphine (Mor 4 mg/kg; ip ---Δ---) at 120 min. Data are expressed as mean±sem (n=16 rats per group). *p<0.05**p<0.01 compared to Veh, ††p<0.01 compared to Mor 4.

FIG. 2 shows a time course response in this model for various test agents. The 300 mg/kg dose of acetaminophen potentiated with 3 mg/kg buspirone HCl demonstrates an analgesic response superior to morphine at 4 mg/kg.

Figure 3:
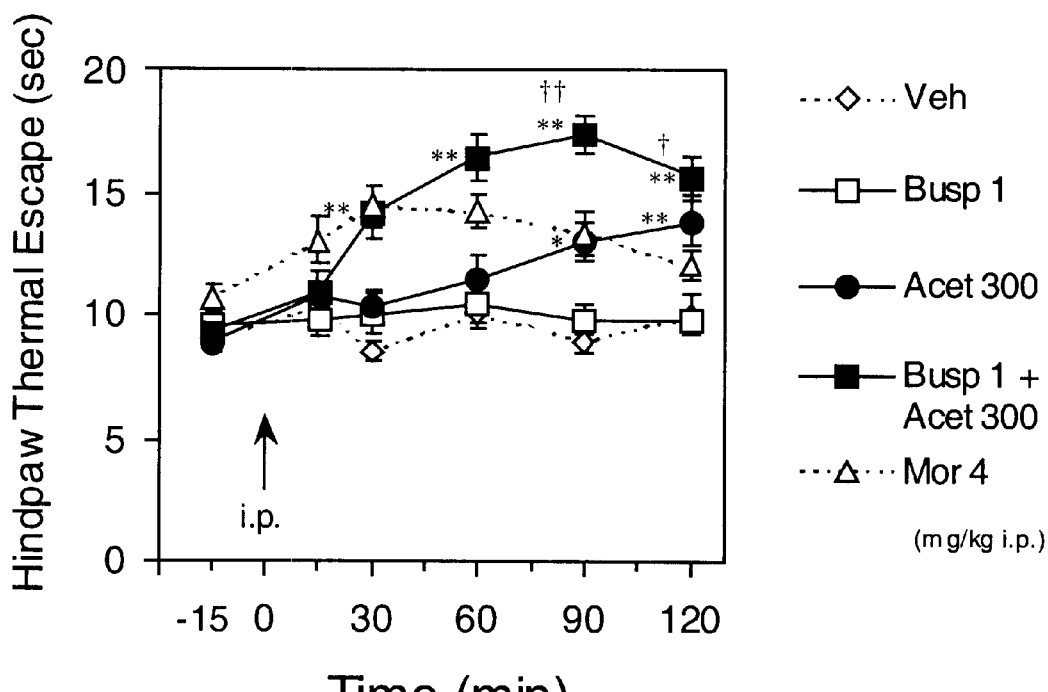
FIG. 3 Coadministration of Buspirone (1 mg/kg; ip) and Acetaminophen (300 mg/kg; ip) produces quicker onset of analgesic action as compared to Acetaminophen alone. The hindpaw thermal escape latency of albino rats was elevated significantly above vehicle (--- ◊ ---) at 90 and 120 min for acetaminophen (Acet 300 mg/kg; ip-●-). When buspirone (Busp 1 mg/kg; ip-□-) was co-administered with acetaminophen (Busp 1+Acet 300 -■-) the analgesic onset was significantly shortened to 30 min post injection giving a more morphine-like response(---Δ---). Efficacy of the combination exceeded that of morphine (Mor 4 mg/kg; ip ---Δ---) at 90 and 120 min. Data are expressed as mean±sem (n=16 rats per group). *p<0.05**p<0.01 compared to Veh, †p<0.05 ††p<0.01 compared to Mor 4.

Potentiating a 300 mg/kg dose of acetaminophen with 1 mg/kg buspirone HCl yields a faster onset of action as shown in FIG. 3.

Figure 4:
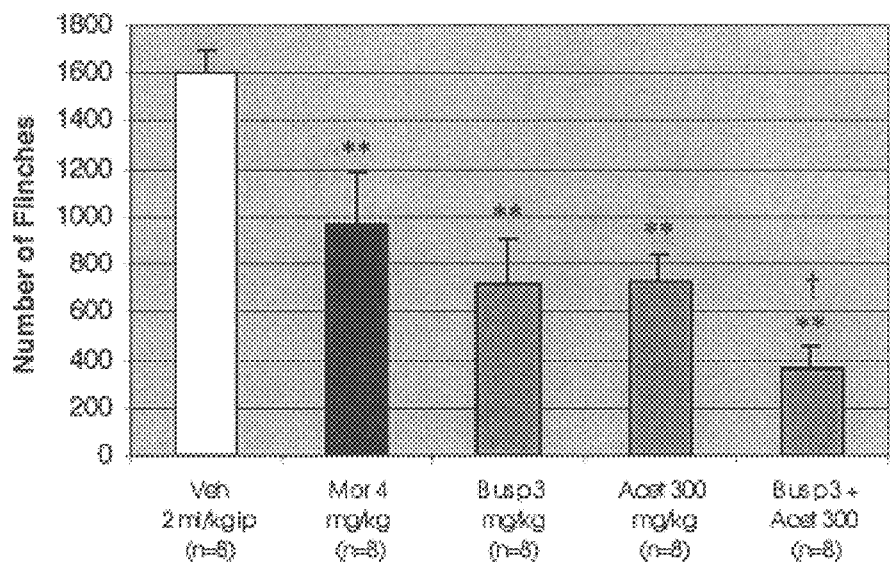
FIG. 4. Coadministration of Buspirone (3 mg/kg) and Acetaminophen (300 mg/kg) produces potent analgesia against chronic pain that is superior to Morphine (4 mg/kg). The formalin-induced flinches of albino rats was significantly suppressed, relative to vehicle (Veh 2 ml/kg ip), by single intraperitoneal delivery of morphine (4 mg/kg), buspirone (Busp 3 mg/kg), or acetaminophen (Acet 300 mg/kg). When buspirone and acetaminophen were coadministered (Busp 3+Acet 300), a even greater suppression of the chronic pain response was observed which was significantly superior to morphine. Data are expressed as mean±sem (n=8 rats per group). **p<0.01 compared to Veh, †p<0.05 compared to Mor 4.

FIG. 4 shows the coadministration of 3 mg/kg buspirone and 300 mg/kg acetaminophen is superior to morphine at 4 mg/kg on a chronic pain test (Formalin Test, Phase II).

Figure 5:
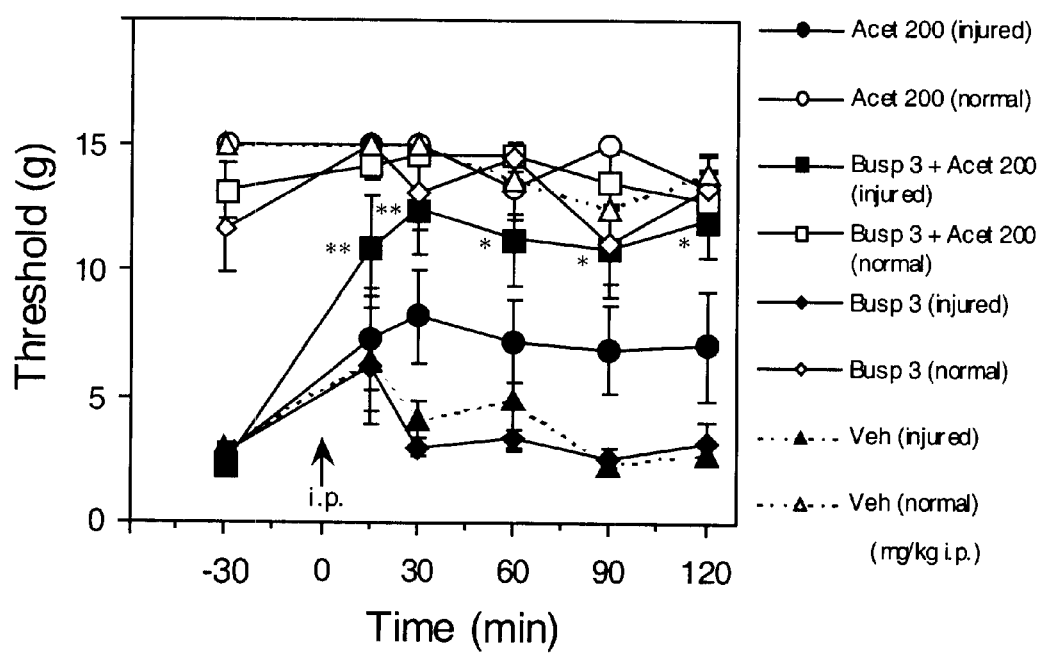
FIG. 5. Coadministration of Buspirone (3 mg/kg) and Acetaminophen (200 mg/kg) produces a rapid (15 min) onset, complete reversal of rat neuropathic pain responses. Following unilateral spinal nerve (L5/L6) ligation (Chung model), vehicle (2 ml/kg ip) treated animals exhibit hypersensitive responses to light touch with a von Frey hair on the injured side (Veh (injured) ---▲---), but not the non-operated side (Veh (normal) ---Δ---) during baseline testing (−30 min). Following drug delivery (at 0 min), none of the compounds produced significant differences in the von Frey thresholds for the normal side (see open symbols -○-, -□-, -◊-) as compared to vehicle (Veh (normal) ---Δ---) at any of the post-injection test times (15, 30, 60, 90 or 120 min). Likewise, for the injured side (filled symbols -●-, -■-, -♦-), treatment with buspirone (3 mg/kg ip; Busp 3 (injured) -♦-) was not significantly different from vehicle (Veh (injured) ---♦---). Although acetaminophen (200 mg/kg ip; Acet 200 (injured) -●-) produced a partial reversal toward normal at 30–120 min, significant differences persisted between the injured (Acet 200 (injured) -●-) and normal (Acet 200 (normal) -○-) sides throughout the study. In contrast, following coadministration of buspirone and acetaminophen (Busp 3+Acet 200), there was a complete reversal of the neuropathic pain responses on the injured side (Busp 3+Acet 200 (injured) -■-), such that differences between the injured -■- and normal -□- side were no longer present. Importantly, this was a rapid onset (beginning at 15 min), long lasting effect (persisted at least 120 min). Data are expressed as mean±sem (n=8 rats per group). **$p<0.01$*$p<0.05$ compared to baseline (−30).

FIG. 5 shows the reversal of neuropathic pain responses in rats treated with 3 mg/kg buspirone and 200 mg/kg acetaminophen.

Figure 6:
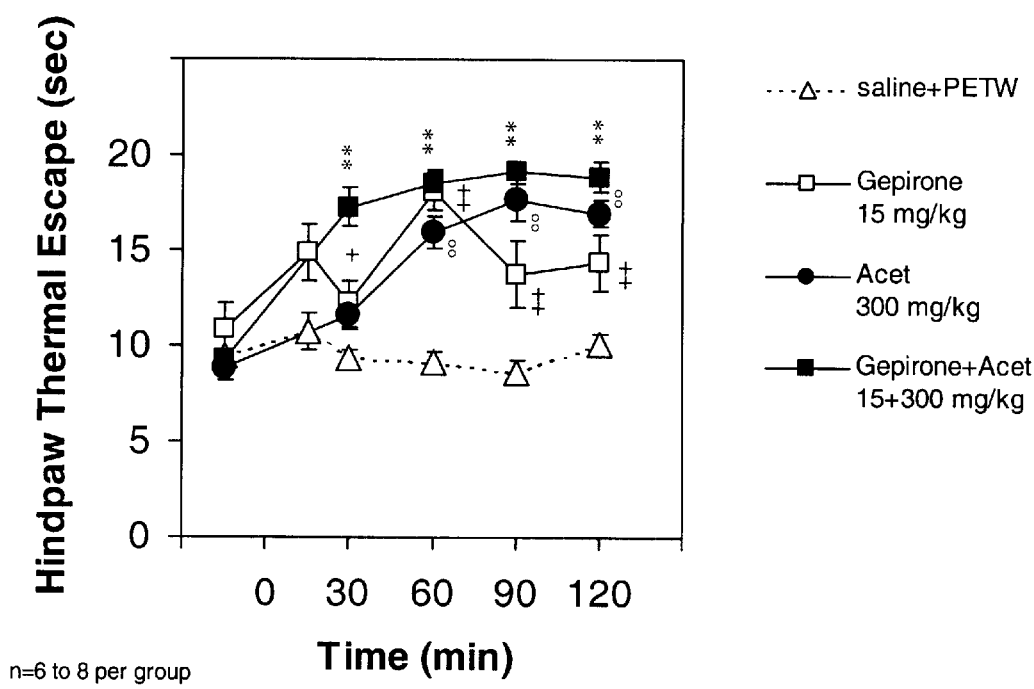
FIG. 6. Coadministration of Gepirone (15 mg/kg) and Acetaminophen (300 mg/kg) produces quicker onset of analgesic action as compared to acetaminophen above. The hindpaw thermal escape latency of albino rats was elevated significantly above that of either gepirone 15 mg/kg) (-□-) or acetaminophen (300 mg/kg) (-●-) alone at 30 min, and was superior to gepirone (15 mg/kg; -□-) alone at 90 and 120 min. Data are expressed as mean±sem (n=6–8 rats per group). */**$p<0.05/0.01$ Gepirone+Acetaminophen. $^{o}/^{oo}p<0.05/0.01$ Acetaminophen+saline. $^{+}/^{++}p<0.5/0.01$ Gepirone+PETW (PEG 400, Ethanol, Tween 80+Water).

FIG. 6 shows more rapid onset of analgesic when a 15 mg/kg dose of the azapirone gepirone HCl is given together with a 300 mg/kg dose of acetaminophen.

Figure 7:
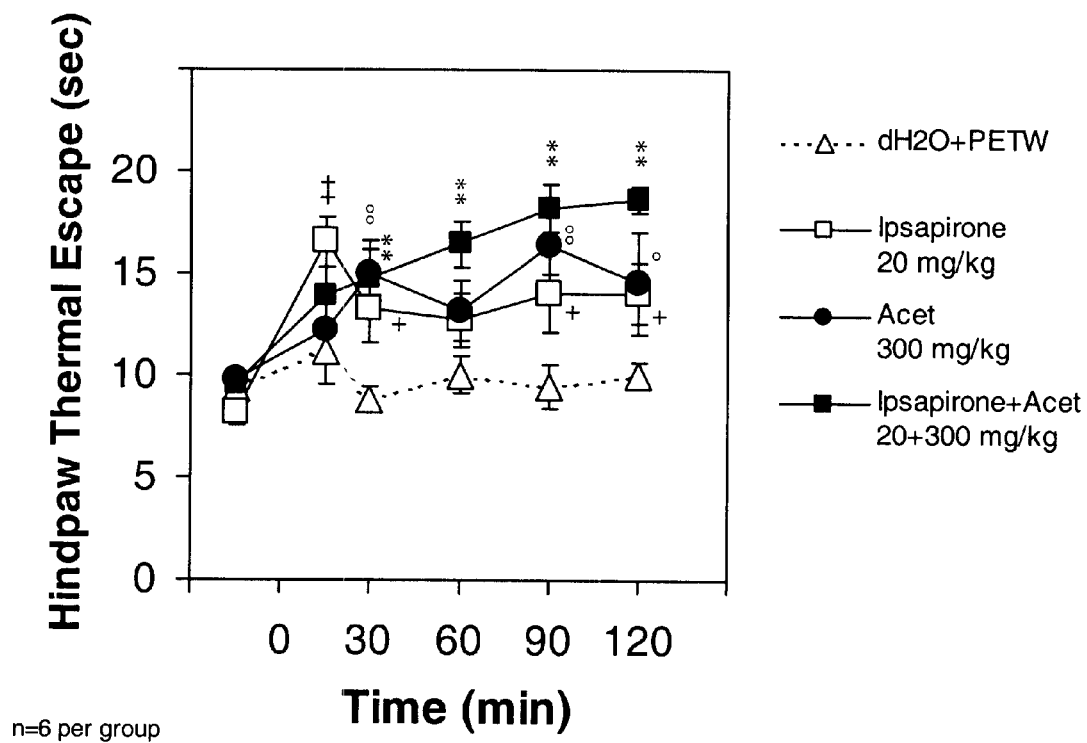
FIG. 7. Coadministration of Ipsapirone (20 mg/kg) and Acetaminophen (300 mg/kg) strengthens the analgesic effect. The hindpaw thermal escape latency of albino rats was elevated significantly above vehicle (---Δ---) throughout the period from 30 min to 120 min when ipsapirone (20 mg/kg; ip -□-) was co-administered with acetaminophen (Ipsapirone+Acet, 20+300 mg/kg; ip -■-). In contrast, for single administration of either ipsapirone alone (20 mg/kg; ip -□-) or acetaminophen alone (300 mg/kg; ip -●-), a comparably high level of analgesia was not consistently attached throughout this same time period. Data are expressed as mean±sem (n=6 rats per group). */**$p<0.05/p<0.01$ ipsapirone+Acetaminophen compared to vehicle (dH2O+PETW). $^{o}/^{oo}p<0.05/p<0.01$ Acetaminophen+dH2O compared to vehicle. $^{+}/^{++}$ $p<0.5/p<0.01$ ipsapirone+PETW compared to vehicle.

FIG. 7 demonstrates an elevation in peak analgesic effect when 20 mg/kg of the azapirone ipsapirone HCl is co-administered with 300 mg/kg of acetaminophen.

Figure 8:
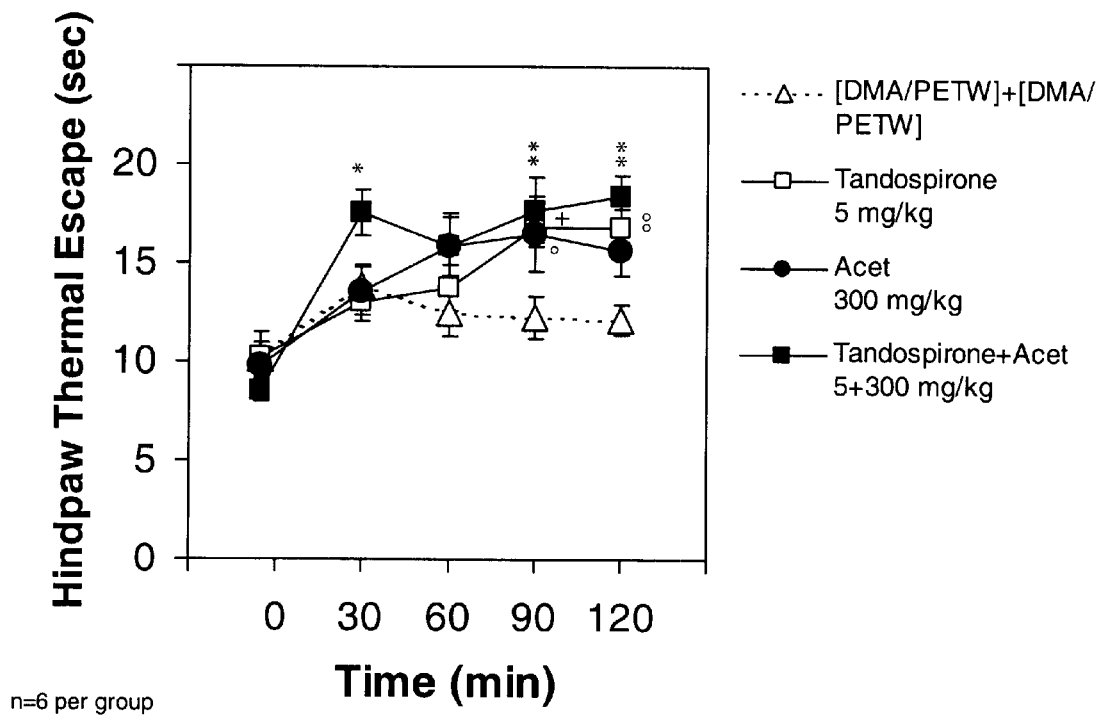
FIG. 8. Coadministration of Tandospirone (5 mg/kg) and Acetaminophen (300 mg/kg) produces more rapid onset of analgesic action compared to acetaminophen alone. The hindpaw thermal escape latency of albino rats was significantly greater than vehicle (DMA/PETW; ip ---Δ---) at 30 min post injection for rats receiving co-administration of tandospirone and acetaminophen (Tandospirone+Acet 5+300; ip -■-). Latencies for single administration of tandospirone alone (Tando+Acet 5+0 mg/kg; ip -□-) or Acetaminophen alone (Tando+Acet 0+300 mg/kg/ip -●-) did not differ from vehicle until 90 min after injection. Data are expressed as mean±sem (n=6 rats per group). */**$p<0.05/p<0.01$ tandospirone+Acetaminophen compared to vehicle (dH2O+PETW). $^{o}/^{oo}p<0.05/p<0.01$ Acetaminophen+dH2O compared to vehicle. $^{+}/^{++}$ $p<0.5/p<0.01$ tandospirone+PETW compared to vehicle. DMA= dimethylacetamide.

FIG. 8 shows earlier onset of analgesia when a 5 mg/kg dose of the azapirone tandospirone HCl is given with a 300 mg/kg dose of acetaminophen as compared to single administration.

These data, taken together, demonstrate that the concurrent administration of an analgesic strengthening amount of an azapirone with a minimally effective acetaminophen dose results in more robust analgesia. In the case of buspirone, this analgesic is faster in onset, more efficacious and has a longer duration of action.

With regard to single agent or combined agent formulations of acetaminophen and azapirone to be employed in the present method, considerable variation in formulations and components may be practiced without departing from the present invention. Any salt form of the azapirone having acceptable formulation properties can be used. However, the HCl salt form of buspirone is preferred.

The present invention then comprises the concurrent administration of a therapeutically effective amount of acetaminophen and an analgesia-strengthening amount of an azapirone such as buspirone or one of its acceptable salts or hydrates.

The present invention also includes pharmaceutical combination compositions comprising the azapirone and acetaminophen components. Such compositions may be in solid or liquid dosage units and may further include suitable pharmaceutical carriers and excipients.

The compositions of this invention may be suitable for administration to an animal. Such animals include both domestic animals; for example, livestock, laboratory animals and household pets, and non-domestic animals such as wildlife. More preferably, the animal is a vertebrate. Most preferably, a compound of this invention shall be administered to a mammal. It is especially preferred that the animal is a domestic mammal or a human. For such purposes, a compound of this invention may be administered as a feed additive.

The most preferred mammal is a human.

Pharmaceutical kit packaging is also envisioned for the present invention. In the kit package are provided both acetaminophen and the azapirone, such as buspirone, each in unit dosage forms for use in the present method.

Dosage and Formulation

Concurrent doses of the azapirone component and acetaminophen component can be given via parenteral, rectal, buccal, transdermal, or, preferably, oral routes of administration by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of standard pharmaceutical practice.

In general, acetaminophen would be administered at levels in accordance with guidelines found in standard medical/drug references such as the *Physicians Desk Reference* and the like. This would be in the range of about 200 to 1300 mg per dose. Amounts of azapirone such as buspirone for concurrent administration would be in the range of from about 0.5 to 30 mg and preferably from 1 to 5 mg per dose.

The dosage administered will, of course, vary depending on the use and known factors such as the age, health, and weight of the recipient; nature and extent of symptoms, concurrent treatments, if any, frequency of treatment, and the effect desired. The recipient may be any type of mammal, but is preferably a human.

In the methods of the present invention, the two compounds, acetaminophen and an azapirone such as buspirone, comprise the active ingredients, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, and the like. Disintegrators include, without limitation, starch, methyl cellulose, agar, bentonite, xanthan gum, and the like.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

The combination products of this invention may be formulated such that, although the active ingredients are combined in a single dosage unit, the physical contact between the active ingredients is minimized. In order to minimize contact, for example, one or more of the active ingredients may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention provides for a combination product wherein one or more of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one or more components is coated with a sustained and/or enteric release polymer, and the other(s) component is also coated with a polymar such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredients are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Specific Embodiments

Pharmaceutical kits or packaging containing separate unit dosage forms of an azapirone such as buspirone and acetaminophen are another aspect of the present invention. Acetaminophen and azapirone dosage forms constituting the combination are packed separately but packaged together as in kit form. Preferably the azapirone and acetaminophen formulations are suited for the same route of administration and are intended to be given concurrently.

Most preferably, the solid oral formulations are contained in packaging materials which protect the formulations from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

All the above-mentioned embodiments of concurrent administration of the acetaminophen and azapirone such as buspirone components are intended for use as an improved method of treating pain. For example, their use is suited for the treatment of articular pain, and in particular in the treatment of arthritis, rheumatoid arthritis, spondylitis, gouty arthritis, osteoarthritis, and juvenile arthritis.

These embodiments can also be used within the context of the treatment of dysmenorrhea, tendinitis, and bursitis. They can also be used in the treatment of pain symptoms of myalgia, dental pain, and migraine, in the treatment of pain of cancerous origin, and also as additional treatments for infectious and febrile states.

Finally, these embodiments can find use in the treatment of neuropathic pain, and in particular of nervous pain, herpes zoster, desafferentation (phantom member) pain, and diabetic neuropathies.

Examples of acetaminophen-azapirone combination pharmaceutical formulations are given below. These examples are intended to be instructive but not exhaustive. Those skilled in the pharmaceutical arts will readily envision alternate formulations applicable to the combination embodiment of the present invention.

The preparation of buspirone can be found in the literature; e.g., see U.S. Pat. No. 3,717,634. Other synthetic processes for buspirone have been disclosed and both buspirone and acetaminophen are available commercially from bulk drug manufacturers.

Similarly, preparation of the other azapirones can also be found in the literature: U.S. Pat. No. 4,423,049 (gepirone); EP 129128 (ipsapirone); U.S. Pat. No. 4,503,303 (tandospirone); and *J. Med. Chem.*, 1988, 31:1382–1392 (zalospirone).

Acetaminophen and azapirone combinations of the present invention may be formulated according to the following non-limiting examples.

The azapirone ingredient is shown as buspirone but it is to be understood that any of the other azapirones could be selected in place of buspirone.

EXAMPLE 1

Gelatine Capsule (Size No. 1)

Acetaminophen . . . 500 mg
Buspirone HCl . . . 2.5 mg
Microcrystalline cellulose . . . 100 mg
Hydroxypropyl methyl cellulose . . . 10 mg for one gelatine capsule

EXAMPLE 2

Gelatine Capsule (Size No. 1)

Acetaminophen . . . 500 mg
Gepirone HCl . . . 5 mg
Microcrystalline cellulose . . . 100 mg
Hydroxypropyl methyl cellulose . . . 10 mg for one gelatine capsule

EXAMPLE 3

Tablet

Acetaminophen . . . 500 mg
Buspirone HCl . . . 5 mg
Microcrystalline cellulose . . . 100 mg
Lactose . . . 100 mg
Hydroxypropyl methyl cellulose . . . 10 mg
Magnesium stearate . . . 5 mg
Hydroxypropyl cellulose . . . 50 mg for one tablet

EXAMPLE 4

Tablet

Acetaminophen . . . 500 mg
Tandospirone HCl . . . 7.5 mg
Microcrystalline cellulose . . . 100 mg
Lactose . . . 100 mg
Hydroxypropyl methyl cellulose . . . 10 mg
Magnesium stearate . . . 5 mg
Hydroxypropyl cellulose . . . 50 mg for one tablet

EXAMPLE 5

Injectable Preparation

Acetaminophen . . . 1000 mg
Buspirone HCl . . . 10 mg
Cysteine . . . 50 mg
PEG 400 . . . 30 mg
Ethyl alcohol . . . 10 mg
Water preparation for injection . . . q.s.p. 100 ml

EXAMPLE 6

Injectable Preparation

Acetaminophen . . . 1000 mg
Zalospirone HCl . . . 12.5 mg
Cysteine . . . 50 mg
PEG 400 . . . 30 mg
Ethyl alcohol . . . 10 mg
Water preparation for injection . . . q.s.p. 100 ml Various modifications of the invention in addition to those shown and described herein will be apparent to those skilled in the art in view of the foregoing description. Such modifications are within the scope of the following claims.

EXAMPLE 7

Suppository

Acetaminophen . . . 1000 mg
Buspirone HCl . . . 20 mg
Semi-synthetic glyceride . . . 2000 mg for one suppository

EXAMPLE 8

Suppository

Acetaminophen . . . 1000 mg
Ipsapirone HCl . . . 20 mg
Semi-synthetic glyceride . . . 2000 mg for one suppository Transdermal delivery vehicles for the azapirone such as buspirone may be suitably adapted for use in the present invention. See WO 97/37659.

EXPERIMENTAL PROCEDURE FOR RAT HINDPAW WITHDRAWAL TEST FOR ANALGESIA (ACUTE PAIN)

To assess the thermally evoked paw-withdrawal response, a commercially available device was used. Specifics of device construction and operation have been published previously (Dirig D M, Salami A, Rathbun M L, Ozaki G T, Yaksh T L. Characterization of variables defining hindpaw withdrawal latency evoked by radiant thermal stimuli. J Neurosci Methods. Oct. 3, 1997; 76(2):183–91). This device is comprised of a glass surface on which the rats were placed individually in Plexiglas cubicles (9×22×25 cm). The surface is maintained at 30° C. by a feedback-controlled, under-glass, forced-air heating system. The thermal nociceptive stimulus originates from a projection bulb below the glass that can be manipulated in a two-dimensional axis on ball bearing slides. This apparatus allows the stimulus to be delivered separately to each hind paw with the aid of an angled mirror mounted on the stimulus source. A timer is actuated with the light source, and escape latency is defined as the time between stimulus onset and the display of a brisk paw withdrawal (detected by photodiode motion sensors that stops the timer and terminates the stimulus; cut-off time for a non-response is 20 sec which triggers automatic termination of the stimulus). In the present study, animals are placed in test boxes for 30 min acclimation and then baseline escape latency is assessed separately for each hindpaw (left and right) at −15 min. All drugs are delivered at 0 min by the intraperitoneal (i.p.) route in a volume of 3 ml/kg. The vehicle for buspirone-HCl (MJ -009022) and morphine sulfate (Sigma, M8777) was 0.9% sodium chloride (Saline). For acetaminophen (Sigma, A7085) the vehicle was 40% polyethylene glycol 400 (PEG-400), 10% EtOH, 15% Tween 80, and 35% deionized H2O (PETW). Acetaminophen was disolved sequentially in two parts: 1) first into a solution of 80% PEG 400+20% EtOH, and 2) then slowly added to it was an equal volume of 30% Tween 80+70% deionized H2O (sonicated as needed). Other azapirone vehicles were Gepirone (saline), ipsapirone (deionized H2O), and tandospirone (DMA+PETW), DMA=5% dimethylacetamide. Each animal received two injections at time zero. Specifically, animals were tested in one of the following 10 treatment conditions (abbreviations used in figures are shown under 'Key" below):

| Cond | Key | Dual Injection (each injected separately; 3 ml/kg; ip) |
|---|---|---|
| a) | Veh | Vehicle + Vehicle (Saline + PETW) |
| b) | Mor 4 | morphine (4 mg/kg) + Saline |
| c) | Busp 1 | buspirone (1 mg/kg) + PETW |
| d) | Busp 3 | buspirone (3 mg/kg) + PETW |
| e) | Acet 100 | acetaminophen (100 mg/kg) + Saline |
| f) | Acet 300 | acetaminophen (300 mg/kg) + Saline |
| g) | 1 + 100 | buspirone (1 mg/kg) + acetaminophen (100 mg/kg) |
| h) | 3 + 100 | buspirone (3 mg/kg) + acetaminophen (100 mg/kg) |
| i) | 1 + 300 | buspirone (1 mg/kg) + acetaminophen (300 mg/kg) |
| j) | 3 + 300 | buspirone (3 mg/kg) + acetaminophen (300 mg/kg) |

Following drug administration, thermal escape latencies are measured at regular intervals (e.g., 15, 30, 60, 90 and 120 min, mean of both paws is used for statistical analysis).

Again, it is understood that the other azapirones are administered in the same manner as buspirone in the above-described testing paradigms.

Preclinical Model of Chronic Pain (Rat Formalin Test)

To assess responses to a chronic stimulus (subcutaneous formalin injection), animals are first placed in clear observation boxes for a 30 min acclimation period prior to testing. Animals are subsequently removed and the dorsum of one hindpaw is injected s.c. with 50 microliters of 2.5% formalin. Animals exhibit a repetitive flicking of the injected paw called 'flinches'. The total number of flinches is computer scored during the chronic phase (10–90 min after formalin) using a commercially available device (George Ozaki, Automated Nocicpetion Analyzer, Department of Anesthesiology, University of California, San Diego; La Jolla, Calif.) which automates the manual procedure described previously by Wheeler-Aceto et al. (Pain 40:229–238, 1990). All drugs are delivered at 30 min prior to formalin injection by the intraperitoneal (i.p.) route in a volume of 2 ml/kg. The vehicle for buspirone-HCl (MJ -009022) and morphine sulfate (Sigma, M8777) was 0.9% sodium chloride (Saline). For acetaminophen (Sigma, A7085) the vehicle was 40% polyethylene glycol 400 (PEG-400), 10% EtOH, 15% Tween 80, and 35% deionized H2O (PETW). Acetaminophen was disolved sequentially in two parts: 1) first into a solution of 80% PEG 400+20% EtOH, and 2) then slowly added to it was an equal volume of 30% Tween 80+70% deionized H2O (sonicated as needed). Each animal received two injections at time zero. Specifically, animals were tested in one of the following 5 treatment conditions (abbreviations used in figures are shown under 'Key" below):

| Cond | Key | Dual Injection (each injected separately; 3 ml/kg; ip) |
|---|---|---|
| a) | Veh | Vehicle + Vehicle (Saline + PETW) |
| b) | Mor 4 | morphine (4 mg/kg) + Saline |
| c) | Busp 3 | buspirone (3 mg/kg) + PETW |
| d) | Acet 300 | acetaminophen (300 mg/kg) + Saline |
| e) | 3 + 300 | buspirone (3 mg/kg) + acetaminophen (300 mg/kg) |

Preclinical Model of Neuropathic Pain (Chung Surgery & Von Frey Test)

To test agents for activity against nerve injury-induced tactile allodynia, animals were surgically prepared with unilateral tight ligation of spinal nerves L5 and L6 following the method of Kim and Chung (1992). See Kim S H, Chung J M. An experimental model for peripheral neuropathy produced by segmental spinal nerve ligation in the rat. Pain. 1992 September;50(3):355–63. After 1–4 weeks recovery, paw withdrawal to light touch was assessed as described by Chaplan et al.(1994). See Chaplan S R, Bach F W, Pogrel J W, Chung J M, Yaksh T L. Quantitative assessment of tactile allodynia in the rat paw. J Neurosci Methods. 1994 July;53 (1):55–63. In brief, rats are placed in a plastic cage with a wire mesh bottom and allowed to acclimate for 30 minutes, until cage exploration and grooming stops. The plantar surface of each hind paw is touched with 1 of a series of von Frey hairs with varying stiffness requiring a known force to buckle. A positive response is noted if the paw is sharply withdrawn. In the present study, after acclimation the baseline von Frey thresholds are assessed for each hindpaw (one normal, one injured) at −30 min. All drugs are delivered at 0 min by the intraperitoneal (i.p.) route in a volume of 2 ml/kg. The vehicle for buspirone-HCl (MJ -009022) and morphine sulfate (Sigma, M8777) was 0.9% sodium chloride (Saline). For acetaminophen (Sigma, A7085) the vehicle was 40% polyethylene glycol 400 (PEG-400), 10% EtOH, 15% Tween 80, and 35% deionized H2O (PETW). Acetaminophen was disolved sequentially in two parts: 1) first into a solution of 80% PEG 400+20% EtOH, and 2) then slowly added to it was an equal volume of 30% Tween 80+70% deionized H2O (sonicated as needed). Each animal received two injections at time zero. Specifically, animals were tested in one of the following 4 treatment conditions (abbreviations used in figures are shown under 'Key" below):

| Cond | Key | Dual Injection (each injected separately; 2 ml/kg; ip) |
|---|---|---|
| a) | Veh | Vehicle + Vehicle (Saline + PETW) |
| b) | Busp 3 | buspirone (3 mg/kg) + PETW |
| c) | Acet 200 | acetaminophen (200 mg/kg) + Saline |
| d) | 3 + 200 | buspirone (3 mg/kg) + acetaminophen (200 mg/kg) |

Following drug administration, von Frey thresholds are measured at 15, 30, 60, 90 and 120 min.

What is claimed is:

1. A method for the treatment of pain by the concurrent administration of acetaminophen and an analgesic strengthening amount of an azapirone selected from buspirone, gepirone, ipsapirone, tandospirone and zalospirone or a pharmaceutically acceptable salt or solvate thereof.

2. The method of claim 1 wherein the hydrochloride salt is the pharmaceutically acceptable salt of the azapirone.

3. The method of claim 1 wherein acetaminophen and the azapirone are administered separately.

4. The method of claim 1 wherein acetaminophen and the azapirone are administered in combination.

5. The method of claim 1 wherein at least 200 to 1300 mg of acetaminophen and at least 0.5 to 30 mg of the azapirone or an acid salt form thereof are administered.

6. A pharmaceutical composition comprising a therapeutically effective amount of acetaminophen and an analgesic strengthening amount of an azapirone or a pharmaceutically acceptable salt thereof.

7. The composition of claim 6 in which the weight ratio of the azapirone to acetaminophen is from 1:5 to 1:2600.

8. The composition of claim 6 in which the weight ratio of the azapirone to acetaminophen is from 1:25 to 1:1000.

9. The composition of claim 6 in which the weight ratio of the azapirone to acetaminophen is from 1:65 to 1:200.

10. The pharmaceutical composition of claim 6 wherein the pharmaceutically acceptable salt of the azapirone is the hydrochloride salt.

11. The pharmaceutical composition of claim 6 in unit dose form.

12. The pharmaceutical composition of claim 7 in unit dose form.

13. The pharmaceutical composition of claim 8 in unit dose form.

14. The pharmaceutical composition of claim 9 in unit dose form.

15. A pharmaceutical kit package containing therapeutically effective dosage forms of acetaminophen and analgesic strengthening dosage forms of an azapirone.

16. The pharmaceutical composition of claim 6 in a formulation suitable for oral administration.

17. The pharmaceutical composition of claim 7 in a formulation suitable for oral administration.

18. The pharmaceutical composition of claim 8 in a formulation suitable for oral administration.

19. The pharmaceutical composition of claim 9 in a formulation suitable for oral administration.

20. The pharmaceutical composition of claim 6 in a formulation suitable for parenteral administration.

21. The pharmaceutical composition of claim 6 in a formulation suitable for transdermal administration.

22. The pharmaceutical composition of claim 6 in a formulation suitable for buccal administration.

23. The pharmaceutical composition of claim 6 in a formulation suitable for rectal administration.

24. The method of claim 1 wherein said pain is chronic pain.

25. The method of claim 1 wherein said pain is acute pain.

26. The method of claim 1 wherein said pain is neuropathic pain.

* * * * *